(12) United States Patent
Plaven et al.

(10) Patent No.: US 7,628,786 B2
(45) Date of Patent: Dec. 8, 2009

(54) UNIVERSAL FOOT SWITCH CONTACT PORT

(75) Inventors: Thomas Plaven, Littleton, CO (US); Robert Lohe, Crofton, MD (US)

(73) Assignee: Covidien AG, Neuhausen Am Rheinfall (CH)

( * ) Notice: Subject to any disclaimer, the term of this patent is extended or adjusted under 35 U.S.C. 154(b) by 459 days.

(21) Appl. No.: 11/129,985

(22) Filed: May 16, 2005

(65) Prior Publication Data

US 2006/0079871 A1    Apr. 13, 2006

Related U.S. Application Data

(60) Provisional application No. 60/666,832, filed on Mar. 31, 2005, provisional application No. 60/618,439, filed on Oct. 13, 2004.

(51) Int. Cl.
*A61B 18/04* (2006.01)
(52) U.S. Cl. .............................. 606/32; 606/1; 439/263; 439/259
(58) Field of Classification Search ..................... 606/4, 606/32–52; 439/13, 19–30, 259, 263, 264, 439/268; 74/411.5; 279/33, 35, 77, 106
See application file for complete search history.

(56) References Cited

U.S. PATENT DOCUMENTS

| 1,787,709 A | 1/1931 | Wappler |
|---|---|---|
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,444,457 A * | 7/1948 | Marks et al. ................. 359/812 |
| 2,827,056 A | 3/1958 | Degelman |
| 2,849,611 A | 8/1958 | Adams |
| 2,883,198 A * | 4/1959 | Narumi ........................ 279/33 |
| 2,916,290 A * | 12/1959 | Skillin ......................... 279/106 |

(Continued)

FOREIGN PATENT DOCUMENTS

DE    179607    3/1905

(Continued)

OTHER PUBLICATIONS

Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.

(Continued)

*Primary Examiner*—Linda C Dvorak
*Assistant Examiner*—Samuel Candler

(57) ABSTRACT

A universal contact port for receiving contacts of various cross-sectional dimensions and cross-sectional profiles of an electrosurgical component is provided. The universal contact port includes a plurality of rollers each defining a corporal axis, the corporal axes being at least substantially parallel to one another; and a plurality of shafts eccentrically supporting a respective roller, each shaft defining a longitudinal axis, wherein each corporal axis is spaced a radial distance from a respective longitudinal axis and wherein the rollers are rotatable about the longitudinal axes. The rollers define an opening therebetween, wherein the opening is expandable and constrictable upon rotation of the rollers about the longitudinal axes, whereby the contact port can accommodate receipt of contacts, from electrosurgical components, of varying cross-sectional diameter therein.

12 Claims, 8 Drawing Sheets

U.S. PATENT DOCUMENTS

| | | | |
|---|---|---|---|
| 2,982,881 A | 5/1961 | Reich | |
| 3,058,470 A | 10/1962 | Seeliger et al. | |
| 3,089,496 A | 5/1963 | Degelman | |
| 3,163,165 A | 12/1964 | Islikawa | |
| 3,252,052 A | 5/1966 | Nash | |
| 3,270,592 A * | 9/1966 | Behnke | 82/117 |
| 3,391,351 A | 7/1968 | Trent | |
| 3,402,326 A | 9/1968 | Guasco et al. | |
| 3,413,480 A | 11/1968 | Biard et al. | |
| 3,436,563 A | 4/1969 | Regitz | |
| 3,439,253 A | 4/1969 | Piteo | |
| 3,439,680 A | 4/1969 | Thomas, Jr. | |
| 3,461,874 A | 8/1969 | Martinez | |
| 3,471,770 A | 10/1969 | Haire | |
| 3,478,744 A | 11/1969 | Leiter | |
| 3,486,115 A | 12/1969 | Anderson | |
| 3,495,584 A | 2/1970 | Schwalm | |
| 3,513,353 A | 5/1970 | Lansch | |
| 3,514,689 A | 5/1970 | Giannamore | |
| 3,515,943 A | 6/1970 | Warrington | |
| 3,518,614 A * | 6/1970 | Nyberg | 439/268 |
| 3,551,786 A | 12/1970 | Van Gulik | |
| 3,562,623 A | 2/1971 | Farnsworth | |
| 3,571,644 A | 3/1971 | Jakoubovitch | |
| 3,589,363 A | 6/1971 | Banko | |
| 3,595,221 A | 7/1971 | Blackett | |
| 3,601,126 A | 8/1971 | Estes | |
| 3,611,053 A | 10/1971 | Rowell | |
| 3,641,422 A | 2/1972 | Farnsworth et al. | |
| 3,662,151 A | 5/1972 | Haffey | |
| 3,675,655 A | 7/1972 | Sittner | |
| 3,683,923 A | 8/1972 | Anderson | |
| 3,693,613 A | 9/1972 | Kelman | |
| 3,697,808 A | 10/1972 | Lee | |
| 3,699,967 A | 10/1972 | Anderson | |
| 3,720,896 A | 3/1973 | Bierlein | |
| 3,743,918 A | 7/1973 | Maitre | |
| 3,766,434 A | 10/1973 | Sherman | |
| 3,768,482 A | 10/1973 | Shaw | |
| 3,783,340 A | 1/1974 | Becker | |
| 3,784,842 A | 1/1974 | Kremer | |
| 3,801,766 A | 4/1974 | Morrison, Jr. | |
| 3,801,800 A | 4/1974 | Newton | |
| 3,812,858 A | 5/1974 | Oringer | |
| 3,815,015 A | 6/1974 | Swin et al. | |
| 3,826,263 A | 7/1974 | Cage et al. | |
| 3,828,768 A | 8/1974 | Douglas | |
| 3,848,600 A | 11/1974 | Patrick, Jr. et al. | |
| 3,870,047 A | 3/1975 | Gonser | |
| 3,875,945 A | 4/1975 | Friedman | |
| 3,885,569 A | 5/1975 | Judson | |
| 3,897,787 A | 8/1975 | Ikuno et al. | |
| 3,897,788 A | 8/1975 | Newton | |
| 3,901,216 A | 8/1975 | Felger | |
| 3,905,373 A | 9/1975 | Gonser | |
| 3,913,583 A | 10/1975 | Bross | |
| 3,923,063 A | 12/1975 | Andrews et al. | |
| 3,933,157 A | 1/1976 | Bjurwill et al. | |
| 3,946,738 A | 3/1976 | Newton et al. | |
| 3,952,748 A | 4/1976 | Kaliher et al. | |
| 3,963,030 A | 6/1976 | Newton | |
| 3,964,487 A | 6/1976 | Judson | |
| 3,971,365 A | 7/1976 | Smith | |
| 3,980,085 A | 9/1976 | Ikuno | |
| 4,005,714 A | 2/1977 | Hilebrandt | |
| 4,024,467 A | 5/1977 | Andrews et al. | |
| 4,041,952 A | 8/1977 | Morrison, Jr. et al. | |
| 4,051,855 A | 10/1977 | Schneiderman | |
| 4,063,557 A | 12/1977 | Wuchinich et al. | |
| 4,074,719 A | 2/1978 | Semm | |
| 4,092,986 A | 6/1978 | Schneiderman | |
| 4,094,320 A | 6/1978 | Newton et al. | |
| 4,102,341 A | 7/1978 | Ikuno et al. | |
| 4,114,623 A | 9/1978 | Meinke et al. | |
| 4,121,590 A | 10/1978 | Gonser | |
| 4,123,673 A | 10/1978 | Gonser | |
| 4,126,137 A | 11/1978 | Archibald | |
| 4,141,616 A * | 2/1979 | Gottlieb | 439/263 |
| 4,145,636 A | 3/1979 | Doi | |
| 4,188,927 A | 2/1980 | Harris | |
| 4,191,188 A | 3/1980 | Belt et al. | |
| 4,192,567 A * | 3/1980 | Gomolka | 439/320 |
| 4,196,734 A | 4/1980 | Harris | |
| 4,200,104 A | 4/1980 | Harris | |
| 4,200,105 A | 4/1980 | Gosner | |
| 4,209,018 A | 6/1980 | Meinke et al. | |
| 4,231,372 A | 11/1980 | Newton | |
| 4,232,676 A | 11/1980 | Herczog | |
| 4,237,887 A | 12/1980 | Gosner | |
| 4,237,891 A | 12/1980 | DuBose et al. | |
| 4,281,373 A | 7/1981 | Mabille | |
| 4,287,557 A | 9/1981 | Brehse | |
| 4,303,073 A | 12/1981 | Archibald | |
| 4,311,154 A | 1/1982 | Sterzer et al. | |
| 4,314,559 A | 2/1982 | Allen | |
| 4,321,926 A | 3/1982 | Roge | |
| 4,334,539 A | 6/1982 | Childs et al. | |
| 4,343,308 A | 8/1982 | Gross | |
| 4,372,315 A | 2/1983 | Shapiro et al. | |
| 4,376,263 A | 3/1983 | Pittroff et al. | |
| 4,378,801 A | 4/1983 | Oosten | |
| 4,384,582 A | 5/1983 | Watt | |
| 4,397,314 A | 8/1983 | Vaguine | |
| 4,407,272 A | 10/1983 | Yamaguchi | |
| 4,411,266 A | 10/1983 | Cosman | |
| 4,416,276 A | 11/1983 | Newton et al. | |
| 4,416,277 A | 11/1983 | Newton et al. | |
| 4,437,464 A | 3/1984 | Crow | |
| 4,452,546 A | 6/1984 | Hiltebrandt et al. | |
| 4,463,759 A | 8/1984 | Garito et al. | |
| 4,470,414 A | 9/1984 | Imagawa et al. | |
| 4,472,661 A | 9/1984 | Culver | |
| 4,474,179 A | 10/1984 | Koch | |
| 4,492,231 A | 1/1985 | Auth | |
| 4,492,832 A | 1/1985 | Taylor | |
| 4,494,541 A | 1/1985 | Archibald | |
| 4,514,619 A | 4/1985 | Kugelman | |
| 4,520,818 A | 6/1985 | Mickiewicz | |
| 4,559,943 A | 12/1985 | Bowers | |
| 4,565,200 A | 1/1986 | Cosman | |
| 4,566,454 A | 1/1986 | Mehl et al. | |
| 4,569,345 A | 2/1986 | Manes | |
| 4,576,177 A | 3/1986 | Webster, Jr. | |
| 4,582,057 A | 4/1986 | Auth et al. | |
| 4,590,934 A | 5/1986 | Malis et al. | |
| 4,608,977 A | 9/1986 | Brown | |
| 4,630,218 A | 12/1986 | Hurley | |
| 4,632,109 A | 12/1986 | Patterson | |
| 4,644,955 A | 2/1987 | Mioduski | |
| 4,646,222 A | 2/1987 | Okado et al. | |
| 4,651,264 A | 3/1987 | Hu | |
| 4,651,280 A | 3/1987 | Chang et al. | |
| 4,657,015 A | 4/1987 | Irnich | |
| 4,658,815 A | 4/1987 | Farin et al. | |
| 4,658,819 A | 4/1987 | Harris et al. | |
| 4,658,820 A | 4/1987 | Klicek | |
| 4,662,383 A | 5/1987 | Sogawa et al. | |
| 4,712,559 A | 12/1987 | Turner | |
| 4,727,874 A | 3/1988 | Bowers et al. | |
| 4,735,204 A | 4/1988 | Sussman et al. | |
| 4,739,759 A | 4/1988 | Rexroth et al. | |
| 4,741,334 A | 5/1988 | Irnich | |
| 4,754,757 A | 7/1988 | Feucht | |
| 4,805,621 A | 2/1989 | Heinze et al. | |

| | | | | | |
|---|---|---|---|---|---|
| 4,818,954 A | 4/1989 | Flachenecker et al. | 5,409,000 A | 4/1995 | Imran |
| 4,827,911 A | 5/1989 | Broadwin et al. | 5,409,006 A | 4/1995 | Buchholtz et al. |
| 4,827,927 A | 5/1989 | Newton | 5,409,485 A | 4/1995 | Suda |
| 4,832,024 A | 5/1989 | Boussignac et al. | 5,413,573 A | 5/1995 | Koivukangas |
| 4,848,335 A | 7/1989 | Manes | 5,417,719 A | 5/1995 | Hull et al. |
| 4,848,355 A | 7/1989 | Nakamura et al. | 5,422,567 A | 6/1995 | Matsunaga |
| 4,860,745 A | 8/1989 | Farin et al. | 5,423,808 A | 6/1995 | Edwards et al. |
| 4,862,889 A | 9/1989 | Feucht | 5,423,809 A | 6/1995 | Klicek |
| 4,880,719 A | 11/1989 | Murofushi et al. | 5,423,810 A | 6/1995 | Goble et al. |
| 4,890,610 A | 1/1990 | Kirwan et al. | 5,430,434 A | 7/1995 | Lederer et al. |
| 4,903,696 A | 2/1990 | Stasz et al. | 5,432,459 A | 7/1995 | Thompson |
| 4,907,589 A | 3/1990 | Cosman | 5,433,739 A | 7/1995 | Sluijter et al. |
| 4,922,210 A | 5/1990 | Flachenecker et al. | 5,434,398 A | 7/1995 | Goldberg |
| 4,931,047 A | 6/1990 | Broadwin et al. | 5,436,566 A | 7/1995 | Thompson |
| 4,931,717 A | 6/1990 | Gray et al. | 5,438,302 A | 8/1995 | Goble |
| 4,938,761 A | 7/1990 | Ensslin | 5,443,463 A | 8/1995 | Stern et al. |
| 4,942,313 A | 7/1990 | Kinzel | 5,445,635 A | 8/1995 | Denen |
| 4,961,047 A | 10/1990 | Carder | 5,451,224 A | 9/1995 | Goble et al. |
| 4,961,435 A | 10/1990 | Kitagawa et al. | 5,458,597 A | 10/1995 | Edwards et al. |
| 4,966,597 A | 10/1990 | Cosman | 5,462,521 A | 10/1995 | Brucker et al. |
| RE33,420 E | 11/1990 | Sussman | 5,472,441 A | 12/1995 | Edwards et al. |
| 4,969,885 A | 11/1990 | Farin | 5,472,443 A | 12/1995 | Cordis et al. |
| 4,993,430 A | 2/1991 | Shimoyama et al. | 5,478,303 A | 12/1995 | Folry-Nolan et al. |
| 4,995,877 A | 2/1991 | Ams et al. | 5,480,399 A | 1/1996 | Hebborn |
| 5,015,227 A | 5/1991 | Broadwin et al. | 5,483,952 A | 1/1996 | Aranyi |
| 5,019,176 A | 5/1991 | Brandhorst, Jr. | 5,490,850 A | 2/1996 | Ellman et al. |
| 5,029,588 A | 7/1991 | Yock et al. | 5,496,312 A | 3/1996 | Klicek |
| 5,087,257 A | 2/1992 | Farin | 5,496,313 A | 3/1996 | Gentelia et al. |
| 5,103,804 A | 4/1992 | Abele et al. | 5,500,012 A | 3/1996 | Brucker et al. |
| 5,108,389 A | 4/1992 | Cosmescu | 5,500,616 A | 3/1996 | Ochi |
| 5,108,391 A | 4/1992 | Flachenecker | 5,514,129 A | 5/1996 | Smith |
| 5,122,137 A | 6/1992 | Lennox | 5,520,684 A | 5/1996 | Imran |
| 5,133,711 A | 7/1992 | Hagen | 5,531,774 A | 7/1996 | Schulman et al. |
| 5,151,102 A | 9/1992 | Kamiyama et al. | 5,534,018 A | 7/1996 | Wahlstrand et al. |
| 5,152,762 A | 10/1992 | McElhenney | 5,536,267 A | 7/1996 | Edwards et al. |
| 5,157,603 A | 10/1992 | Scheller et al. | 5,540,681 A | 7/1996 | Strul et al. |
| 5,160,334 A | 11/1992 | Billings et al. | 5,540,683 A | 7/1996 | Ichikawa |
| 5,162,217 A | 11/1992 | Hartman | 5,540,684 A | 7/1996 | Hassler, Jr. |
| 5,167,658 A | 12/1992 | Ensslin | 5,540,724 A | 7/1996 | Cox |
| 5,190,517 A | 3/1993 | Zieve et al. | 5,556,396 A | 9/1996 | Cohen et al. |
| 5,196,008 A | 3/1993 | Kuenecke | 5,558,671 A | 9/1996 | Yates |
| 5,196,009 A | 3/1993 | Kirwan, Jr. | 5,569,242 A | 10/1996 | Lax et al. |
| 5,201,900 A | 4/1993 | Nardella | 5,571,147 A | 11/1996 | Sluijter et al. |
| 5,207,691 A | 5/1993 | Nardella | 5,573,533 A | 11/1996 | Strul |
| 5,230,623 A | 7/1993 | Guthrie et al. | 5,588,432 A | 12/1996 | Crowley |
| 5,233,515 A | 8/1993 | Cosman | 5,594,636 A | 1/1997 | Schauder |
| 5,267,994 A | 12/1993 | Gentelia et al. | 5,596,466 A | 1/1997 | Ochi |
| 5,267,997 A | 12/1993 | Farin | 5,599,344 A | 2/1997 | Paterson |
| 5,281,213 A | 1/1994 | Milder et al. | 5,599,345 A | 2/1997 | Edwards et al. |
| 5,300,068 A | 4/1994 | Rosar et al. | 5,605,150 A | 2/1997 | Radons et al. |
| 5,300,070 A | 4/1994 | Gentelia | 5,613,966 A | 3/1997 | Makower et al. |
| 5,318,563 A | 6/1994 | Malis et al. | 5,613,996 A | 3/1997 | Lindsay |
| 5,323,778 A | 6/1994 | Kandarpa et al. | 5,625,370 A | 4/1997 | D'Hont |
| 5,324,283 A | 6/1994 | Heckele | 5,626,575 A | 5/1997 | Crenner |
| 5,330,518 A | 7/1994 | Neilson et al. | 5,628,745 A | 5/1997 | Bek |
| 5,334,193 A | 8/1994 | Nardella | 5,643,330 A | 7/1997 | Holsheimer et al. |
| 5,341,807 A | 8/1994 | Nardella | 5,647,869 A | 7/1997 | Goble et al. |
| 5,342,356 A | 8/1994 | Ellman | 5,647,871 A | 7/1997 | Levine et al. |
| 5,342,357 A | 8/1994 | Nardella | 5,651,780 A | 7/1997 | Jackson et al. |
| 5,342,409 A | 8/1994 | Mullett | 5,658,322 A | 8/1997 | Fleming |
| 5,348,554 A | 9/1994 | Imran et al. | 5,660,567 A | 8/1997 | Nierlich et al. |
| 5,370,645 A | 12/1994 | Klicek et al. | 5,688,267 A | 11/1997 | Panescu et al. |
| 5,370,672 A | 12/1994 | Fowler et al. | 5,690,692 A | 11/1997 | Fleming |
| 5,370,675 A | 12/1994 | Edwards et al. | 5,693,042 A | 12/1997 | Bioarski et al. |
| 5,372,596 A | 12/1994 | Klicek et al. | 5,695,494 A | 12/1997 | Becker |
| 5,383,874 A | 1/1995 | Jackson et al. | 5,696,351 A | 12/1997 | Benn et al. |
| 5,383,876 A | 1/1995 | Nardella | 5,702,386 A | 12/1997 | Stern et al. |
| 5,383,917 A | 1/1995 | Desai et al. | 5,702,429 A | 12/1997 | King |
| 5,385,148 A | 1/1995 | Lesh et al. | 5,707,369 A | 1/1998 | Vaitekunas et al. |
| 5,396,062 A | 3/1995 | Eisentraut et al. | 5,713,896 A | 2/1998 | Nardella |
| 5,400,267 A | 3/1995 | Denen et al. | 5,720,744 A | 2/1998 | Eggleston et al. |
| 5,403,311 A | 4/1995 | Abele et al. | 5,722,975 A | 3/1998 | Edwards et al. |
| 5,403,312 A | 4/1995 | Yates et al. | 5,733,281 A | 3/1998 | Nardella |

| | | | | | | |
|---|---|---|---|---|---|---|
| 5,749,869 | A | 5/1998 | Lindenmeier et al. | 6,273,886 B1 | 8/2001 | Edwards |
| 5,749,871 | A | 5/1998 | Hood et al. | 6,275,786 B1 | 8/2001 | Daners |
| 5,755,715 | A | 5/1998 | Stern | 6,293,941 B1 | 9/2001 | Strul |
| 5,766,165 | A | 6/1998 | Gentelia et al. | 6,293,942 B1 | 9/2001 | Goble et al. |
| 5,769,847 | A | 6/1998 | Panescu | 6,306,131 B1 | 10/2001 | Hareyama et al. |
| 5,772,659 | A | 6/1998 | Becker et al. | 6,306,134 B1 | 10/2001 | Goble et al. |
| 5,792,138 | A | 8/1998 | Shipp | 6,309,386 B1 | 10/2001 | Bek |
| 5,797,802 | A | 8/1998 | Nowak | 6,337,998 B1 | 1/2002 | Behl et al. |
| 5,797,902 | A | 8/1998 | Netherly | 6,338,657 B1 | 1/2002 | Harper et al. |
| 5,814,092 | A | 9/1998 | King | 6,358,245 B1 | 3/2002 | Edwards |
| 5,817,093 | A | 10/1998 | Williamson, IV et al. | 6,364,877 B1 | 4/2002 | Goble et al. |
| 5,820,568 | A | 10/1998 | Willis | 6,383,183 B1 | 5/2002 | Sekino et al. |
| 5,827,271 | A | 10/1998 | Bussey et al. | 6,398,779 B1 | 6/2002 | Buysse et al. |
| 5,830,212 | A | 11/1998 | Cartmell | 6,398,781 B1 | 6/2002 | Goble et al. |
| 5,836,943 | A | 11/1998 | Miller, III | 6,402,741 B1 | 6/2002 | Keppel et al. |
| 5,836,990 | A | 11/1998 | Li | 6,402,743 B1 | 6/2002 | Orszulak et al. |
| 5,846,236 | A | 12/1998 | Lindenmeier et al. | 6,416,509 B1 | 7/2002 | Goble et al. |
| 5,868,737 | A | 2/1999 | Taylor et al. | 6,436,096 B1 | 8/2002 | Hareyama |
| 5,868,739 | A | 2/1999 | Lindenmeier et al. | 6,451,015 B1 | 9/2002 | Rittman, III et al. |
| 5,868,740 | A | 2/1999 | LeVeen et al. | 6,458,121 B1 | 10/2002 | Rosenstock |
| 5,871,481 | A | 2/1999 | Kannenberg et al. | 6,464,689 B1 | 10/2002 | Qin |
| 5,897,552 | A | 4/1999 | Edwards et al. | 6,464,696 B1 | 10/2002 | Oyama |
| 5,908,444 | A | 6/1999 | Azure | 6,506,189 B1 | 1/2003 | Rittman, III et al. |
| 5,913,882 | A | 6/1999 | King | 6,508,815 B1 | 1/2003 | Strul |
| 5,921,982 | A | 7/1999 | Lesh et al. | 6,511,476 B2 | 1/2003 | Hareyama |
| 5,925,070 | A | 7/1999 | King et al. | 6,547,786 B1 | 4/2003 | Goble |
| 5,931,836 | A | 8/1999 | Hatta et al. | 6,558,376 B2 | 5/2003 | Bishop |
| 5,938,690 | A | 8/1999 | Law et al. | 6,562,037 B2 | 5/2003 | Paton |
| 5,948,007 | A | 9/1999 | Starkenbaum et al. | 6,565,559 B2 | 5/2003 | Eggleston |
| 5,951,545 | A | 9/1999 | Schilling | 6,573,248 B2 | 6/2003 | Ramasamy et al. |
| 5,951,546 | A | 9/1999 | Lorentzen | 6,575,969 B1 | 6/2003 | Rittman, III et al. |
| 5,954,686 | A | 9/1999 | Garito et al. | 6,582,427 B1 | 6/2003 | Goble et al. |
| 5,954,717 | A | 9/1999 | Behl et al. | 6,620,157 B1 | 9/2003 | Dabney et al. |
| 5,961,344 | A | 10/1999 | Rosales et al. | 6,623,423 B2 | 9/2003 | Sakurai |
| 5,971,980 | A | 10/1999 | Sherman | 6,635,057 B2 | 10/2003 | Harano |
| 5,976,128 | A | 11/1999 | Schilling et al. | 6,648,883 B2 | 11/2003 | Francischelli |
| 5,983,141 | A | 11/1999 | Sluijter et al. | 6,652,514 B2 | 11/2003 | Ellman |
| 6,010,499 | A | 1/2000 | Cobb | 6,663,623 B1 | 12/2003 | Oyama et al. |
| 6,014,581 | A | 1/2000 | Whayne et al. | 6,663,624 B2 | 12/2003 | Edwards |
| 6,033,399 | A | 3/2000 | Gines | 6,666,860 B1 | 12/2003 | Takahashi |
| 6,044,283 | A | 3/2000 | Fein et al. | 6,679,875 B2 | 1/2004 | Honda |
| 6,053,910 | A | 4/2000 | Fleenor | 6,682,527 B2 | 1/2004 | Strul |
| 6,053,912 | A | 4/2000 | Panescu et al. | 6,685,700 B2 | 2/2004 | Behl |
| 6,056,745 | A | 5/2000 | Panescu et al. | 6,685,701 B2 | 2/2004 | Orszulak et al. |
| 6,056,746 | A | 5/2000 | Goble et al. | 6,692,489 B1 | 2/2004 | Heim |
| 6,063,075 | A | 5/2000 | Mihori | 6,712,813 B2 | 3/2004 | Ellman |
| 6,063,078 | A | 5/2000 | Wittkampf | 6,730,080 B2 | 5/2004 | Harano |
| 6,068,627 | A | 5/2000 | Orszulak et al. | 6,733,495 B1 | 5/2004 | Bek |
| 6,074,386 | A | 6/2000 | Goble et al. | 6,733,498 B2 | 5/2004 | Paton |
| 6,080,149 | A | 6/2000 | Huang et al. | 6,740,079 B1 | 5/2004 | Eggers |
| 6,093,186 | A | 7/2000 | Goble | 6,740,085 B2 | 5/2004 | Hareyama |
| RE36,871 | E | 9/2000 | Epstein | 6,783,523 B2 | 8/2004 | Qin |
| 6,113,591 | A | 9/2000 | Whayne et al. | 6,790,206 B2 | 9/2004 | Panescu |
| 6,113,596 | A | 9/2000 | Hooven | 6,796,981 B2 | 9/2004 | Wham |
| 6,123,702 | A | 9/2000 | Swanson et al. | 6,824,539 B2 | 11/2004 | Novak |
| 6,132,429 | A | 10/2000 | Baker | 6,830,569 B2 | 12/2004 | Thompson |
| 6,142,992 | A | 11/2000 | Cheng et al. | 6,843,789 B2 | 1/2005 | Goble |
| 6,162,217 | A | 12/2000 | Kannenberg et al. | 6,849,073 B2 | 2/2005 | Hoey |
| 6,203,541 | B1 | 3/2001 | Keppel | 6,855,141 B2 | 2/2005 | Lovewell |
| 6,210,403 | B1 | 4/2001 | Klicek | 6,855,142 B2 | 2/2005 | Harano |
| 6,228,080 | B1 | 5/2001 | Gines | 6,860,881 B2 | 3/2005 | Sturm |
| 6,228,081 | B1 | 5/2001 | Goble | 6,864,686 B2 | 3/2005 | Novak |
| 6,231,569 | B1 | 5/2001 | Bek | 6,875,210 B2 | 4/2005 | Refior |
| 6,235,020 | B1 | 5/2001 | Cheng et al. | 6,893,435 B2 | 5/2005 | Roane |
| 6,238,387 | B1 | 5/2001 | Miller, III | 2001/0014804 A1 | 8/2001 | Goble et al. |
| 6,238,388 | B1 | 5/2001 | Ellman | 2001/0031962 A1 | 10/2001 | Eggleston |
| 6,241,725 | B1 | 6/2001 | Cosman | 2002/0035363 A1 | 3/2002 | Edwards et al. |
| 6,245,065 | B1 | 6/2001 | Panescu | 2002/0035364 A1 | 3/2002 | Schoenman et al. |
| 6,246,912 | B1 | 6/2001 | Sluijter et al. | 2002/0068932 A1 | 6/2002 | Edwards |
| 6,251,106 | B1 | 6/2001 | Becker et al. | 2002/0193787 A1 | 12/2002 | Qin |
| 6,258,085 | B1 | 7/2001 | Eggleston | 2003/0004510 A1 | 1/2003 | Wham et al. |
| 6,261,285 | B1 | 7/2001 | Novak | 2003/0013350 A1 | 1/2003 | D'Addario |
| 6,261,286 | B1 | 7/2001 | Goble et al. | 2003/0060818 A1 | 3/2003 | Kannenberg |

| | | | |
|---|---|---|---|
| 2003/0078572 A1 | 4/2003 | Pearson et al. | |
| 2003/0139741 A1 | 7/2003 | Goble et al. | |
| 2003/0153908 A1 | 8/2003 | Goble | |
| 2003/0163123 A1 | 8/2003 | Goble | |
| 2003/0163124 A1 | 8/2003 | Goble | |
| 2003/0171745 A1 | 9/2003 | Francischelli | |
| 2003/0199863 A1 | 10/2003 | Swanson | |
| 2004/0002745 A1 | 1/2004 | Flemming | |
| 2004/0015163 A1 | 1/2004 | Buysse et al. | |
| 2004/0019347 A1 | 1/2004 | Sakurai | |
| 2004/0024395 A1 | 2/2004 | Ellman | |
| 2004/0030328 A1 | 2/2004 | Eggers | |
| 2004/0044339 A1 | 3/2004 | Beller | |
| 2004/0049179 A1 | 3/2004 | Francischelli | |
| 2004/0054365 A1 | 3/2004 | Goble | |
| 2004/0059323 A1 | 3/2004 | Sturm et al. | |
| 2004/0068304 A1 | 4/2004 | Paton | |
| 2004/0082946 A1 | 4/2004 | Malis | |
| 2004/0097117 A1* | 5/2004 | Gonnering | 439/218 |
| 2004/0097912 A1 | 5/2004 | Gonnering | |
| 2004/0097914 A1 | 5/2004 | Pantera | |
| 2004/0097915 A1 | 5/2004 | Refior | |
| 2004/0116919 A1 | 6/2004 | Heim | |
| 2004/0130104 A1* | 7/2004 | Sundkvist | 279/35 |
| 2004/0133189 A1 | 7/2004 | Sakurai | |
| 2004/0138653 A1 | 7/2004 | Dabney et al. | |
| 2004/0138654 A1 | 7/2004 | Goble | |
| 2004/0147918 A1 | 7/2004 | Keppel | |
| 2004/0167508 A1 | 8/2004 | Wham et al. | |
| 2004/0172016 A1 | 9/2004 | Bek | |
| 2004/0182972 A1 | 9/2004 | Bakos et al. | |
| 2004/0193148 A1 | 9/2004 | Wham et al. | |
| 2004/0230189 A1 | 11/2004 | Keppel | |
| 2004/0236323 A1 | 11/2004 | Schoenman et al. | |
| 2004/0243120 A1 | 12/2004 | Orszulak et al. | |
| 2004/0260279 A1 | 12/2004 | Goble | |
| 2005/0004564 A1 | 1/2005 | Wham | |
| 2005/0013675 A1* | 1/2005 | Bengston et al. | 409/231 |
| 2005/0021020 A1 | 1/2005 | Blaha et al. | |
| 2005/0021022 A1 | 1/2005 | Sturm et al. | |
| 2005/0101951 A1 | 5/2005 | Wham | |
| 2005/0113818 A1 | 5/2005 | Sartor | |
| 2005/0113819 A1 | 5/2005 | Wham | |
| 2005/0149151 A1 | 7/2005 | Orszulak | |
| 2005/0182398 A1 | 8/2005 | Paterson | |
| 2005/0197659 A1 | 9/2005 | Bahney | |
| 2005/0203504 A1 | 9/2005 | Wham et al. | |
| 2006/0025760 A1 | 2/2006 | Podhajsky | |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 19717411 | 11/1998 |
| DE | 19717411 A1 | 11/1998 |
| EP | 246350 | 11/1987 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 878169 | 11/1998 |
| EP | 1293171 | 3/2003 |
| FR | 1275415 | 10/1961 |
| FR | 1347865 | 11/1963 |
| FR | 2313708 | 12/1976 |
| FR | 2502935 | 10/1982 |
| FR | 2517953 | 6/1983 |
| FR | 2573301 | 5/1986 |
| GB | 607850 | 9/1948 |
| GB | 855459 | 11/1960 |
| GB | 902775 | 8/1962 |
| GB | 2164473 | 3/1986 |
| GB | 2214430 | 9/1989 |
| SU | 166452 | 1/1965 |
| SU | 727201 | 4/1980 |
| WO | WO92/06642 | 4/1992 |
| WO | WO93/24066 | 12/1993 |
| WO | WO94/24949 | 11/1994 |
| WO | WO94/28809 | 12/1994 |
| WO | WO95/09577 | 4/1995 |
| WO | WO95/19148 | 7/1995 |
| WO | WO96/02180 | 2/1996 |
| WO | WO96/04860 | 2/1996 |
| WO | WO96/08794 | 3/1996 |
| WO | WO96/18349 | 6/1996 |
| WO | WO96/29946 | 10/1996 |
| WO | WO96/39914 | 12/1996 |
| WO | WO97/06739 | 2/1997 |
| WO | WO97/06740 | 2/1997 |
| WO | WO97/06855 | 2/1997 |
| WO | WO97/17029 | 5/1997 |
| WO | WO 00/33753 | 6/2000 |
| WO | WO02/11634 | 2/2002 |
| WO | WO02/45589 | 6/2002 |
| WO | WO02/47565 | 6/2002 |
| WO | WO02/088128 | 7/2002 |
| WO | WO03/092520 | 11/2003 |
| WO | WO2004/028385 | 4/2004 |
| WO | WO2005/046496 | 5/2005 |
| WO | WO2005/048809 | 6/2005 |
| WO | WO2005/050151 | 6/2005 |

OTHER PUBLICATIONS

Anderson et al., "A Numerical Study of Rapid Heating for High Temperature Radio Frequency Hyperthermia" International Journal of Bio-Medical Computing, 35 (1994) pp. 297-307.

Astrahan, "A Localized Current Field Hyperthermia System for Use with 192-Iridium Interstitial Implants" Medical Physics, 9 (3), May/Jun. 1982.

Bergdahl et al., "Studies on Coagulation and the Development of an Automatic computerized Bipolar Coagulator" Journal of Neurosurgery 75:1, (Jul. 1991) pp. 148-151.

Chicharo et al. "A Sliding Goertzel Algorith" Aug. 1996, pp. 283-297 Signal Processing, Elsevier Science Publishers B.V. Amsterdam, NL vol. 52 No. 3.

Cosman et al., "Methods of Making Nervous System Lesions" In William RH, Rengachary SS (eds): Neurosurgery, New York: McGraw-Hill, vol. 111, (1984), pp. 2490-2499.

Cosman et al., "Radiofrequency Lesion Generation and Its Effect on Tissue Impedance" Applied Neurophysiology 51: (1988) pp. 230-242.

Cosman et al., "Theoretical Aspects of Radiofrequency Lesions in the Dorsal Root Entry Zone" Neurosurgery 15:(1984) pp. 945-950.
Geddes et al., "The Measurement of Physiologic Events by Electrical Impedence" Am. J. MI, Jan. Mar. 1964, pp. 16-27.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure "The O.R. Pro 300" 1 p.
Ogden Goertzel Alternative to the Fourier Transform: Jun. 1993 pp. 485-487 Electronics World; Reed Business Publishing, Sutton, Surrey, BG vol. 99, No. 9. 1687.
Sugita et al., "Bipolar Coagulator with Automatic Thermocontrol" J. Neurosurg., vol. 41, Dec. 1944, pp. 777-779.
Valleylab Brochure "Valleylab Electroshield Monitoring System" 2 pp.
Vallfors et al., "Automatically Controlled Bipolar Electrosoagulation-'COA-COMP" Neurosurgical Review 7:2-3 (1984) pp. 187-190.
Wald et al., "Accidental Burns". JAMA, Aug. 16, 1971, vol. 217, No. 7, pp. 916-921.
Richard Wolf Medical Instruments Corp. Brochure, "Kleppinger Bipolar Forceps & Bipolar Generator" 3 pp.
International Search Report PCT/US03/37110.
International Search Report PCT/US03/37310.
International Search Report EP 04009964.
International Search Report EP 98300964.8.
International Search Report EP 04015981.6.
Medtrex Brochure "The O.R. Pro 300" 1 p. Sep. 1998.
Valleylab Brochure "Valleylab Electroshield Monitoring System" 2 pp. Nov. 1995.
Richard Wolf Medical Instruments Corp. Brochure, "Kleppinger Bipolar Forceps & Bipolar Generator" 3 pp. Jan. 1989.
Bergdahl et al. "Studies on Coagulation and the Development of an Automatic Computerized Bipolar Coagulator" J.Neurosurg, vol. 75, Jul. 1991, pp. 148-151.
International Search Report PCT/US03/37110 dated Jul. 25, 2005.
International Search Report PCT/US03/37310 dated Aug. 13, 2004.
International Search Report EP 04009964 dated Jul. 13, 2004.
International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report, International Application No. PCT/US2008/058929, dated Aug. 1, 2008.

* cited by examiner

UNIVERSAL FOOT SWITCH CONTACT PORT

CROSS-REFERENCE TO RELATED APPLICATION

The present application claims the benefit of and priority to U.S. Provisional Application 60/618,439, filed on Oct. 13, 2004, and U.S. Provisional Application 60/666,832, filed on Mar. 31, 2005, the entire contents of each of which being incorporated herein by reference.

BACKGROUND

1. Technical Field

The present disclosure relates to electrosurgical instrument systems and, more particularly, to a universally adaptable contact port for selectively connecting electrosurgical instruments to electrosurgical generators.

2. Background

Electrosurgical instrument systems have become widely used by surgeons in recent years. Accordingly, a need has developed for equipment that is easy to handle and operate, is reliable and is safe. By and large, most electrosurgical instrument systems typically include a hand-held electrosurgical instrument or pencil electrically connected to a source of electrosurgical energy (e.g., an electrosurgical generator). When activated, the electrosurgical instrument transfers electrosurgical energy, e.g., radio-frequency (RF) electrical energy, to a tissue site to treat tissue. The electrosurgical energy is returned to the electrosurgical generator via a return electrode (i.e., for use with a bipolar system) or a return electrode pad positioned under a patient (i.e., for use with a monopolar system configuration). The waveforms produced by the electrosurgical generator yield a predetermined electrosurgical effect which can be used to cauterize, ablate, coagulate or seal tissue depending upon a particular surgical purpose.

Electrosurgical instrument systems are typically provided with electrosurgical activation components (e.g., a remote hand switch or foot switch), operatively connected (e.g., hard wired) to the electrosurgical generator, which allows a user to selectively control the application of the electrosurgical energy to the electrosurgical instrument. In the past, surgeons connected the electrical components or instruments using so-called "banana plugs" or "flying leads". Recently, electrosurgical instrument systems are increasingly being provided with coupling and/or connecting systems (e.g., a plug) for removably connecting the electrosurgical instrument components and/or the electrosurgical activation components to the electrosurgical generator. Typically, the electrosurgical instrument and/or activation component is provided with a so called "male" connector while the electrosurgical generator is provided with the corresponding "female" receptacle.

As can be appreciated, electrosurgical instruments and/or activation components manufactured by different manufacturers are provided with active contacts having different diameters, e.g., from about 2 mm to about 10 mm making it difficult to use particular instruments with particular generators. As such, components can only be plugged into receptacles having correspondingly sized apertures provided therein or the surgeon has to couple an adapter to the instrument prior to use. Depending upon the number of instruments being used with a particular generator might make the task of providing an appropriate adapter time consuming.

Accordingly, a need exists for a universal contact port for electrosurgical generators which allows components having various sized active contacts to be selectively connected thereto.

SUMMARY

According to an embodiment, a universal contact port for use in an electrosurgical generator is provided. The contact port includes a ring gear having a circular rim formed therein and defining a central rotational axis, the rim including a series of teeth formed therearound; a plurality of spur gears operatively engaged with the rim of the ring gear, each spur gear defining a longitudinal axis which is at least substantially parallel with the central rotational axis; and a plurality of rollers operatively associated with a respective spur gear, each roller defining a corporal axis. The corporal axis of each roller is parallel to and spaced from the longitudinal axis of the respective spur gear. The rollers define an opening therebetween. The opening is constricted by rotation of the ring gear in a first direction about the central rotational axis and expanded by rotation of the ring gear in a direction opposite to the first direction.

The universal contact port may further include a plurality of shafts for eccentrically supporting each roller. Each shaft may include a first end operatively associated with a respective spur gear and a second end operatively associated with the electrosurgical generator.

It is envisioned that three rollers are provided. The shafts of the three rollers may be equally spaced from one another. The opening is at a minimum when the rollers are in contact with one another. The opening is at a maximum when the corporal axes of the rollers are positioned radially outward of the longitudinal axes of the shafts relative to the central axis of the ring gear. The opening is expandable to receive active contacts of varying diameters therein. The opening is sizable to receive contacts having cross-sectional diameters from about 2 mm to about 10 mm.

The rollers may be fabricated from electrically conductive material. The shafts, the spur gears and the ring gears may be fabricated from electrically conductive material.

The ring gear and the spur gears define a planetary gear system.

The universal contact port further includes at least one biasing member operatively associated with at least one of the ring gear, at least one of the spur gears and at least one of the rollers for urging the rollers into contact with one another.

According to another aspect of the present disclosure, a universal contact port for receiving contacts of various cross-sectional dimensions and cross-sectional profiles of an electrosurgical component is provided. The universal contact port includes a plurality of rollers each defining a corporal axis, the corporal axes being at least substantially parallel to one another; and a plurality of shafts eccentrically supporting a respective roller, each shaft defining a longitudinal axis, wherein each corporal axis is spaced a radial distance from a respective longitudinal axis and wherein the rollers are rotatable about the longitudinal axes. The rollers define an opening therebetween. The opening is expandable and constrictable upon rotation of the rollers about the longitudinal axes. The contact port can accommodate receipt of contacts, from electrosurgical components, of varying cross-sectional diameter therein.

The opening may have a minimum cross-sectional dimension when the rollers are in contact with one another. The opening may have a maximum cross-sectional profile when the corporal axes of the rollers are radially aligned with respective longitudinal axes of the shafts.

The universal contact port further includes a spur gear operatively associated with an end of each of the shafts; and a drive member operatively associated with all the spur gears for transmitting rotation to each of the spur gear simultaneously. The drive member may be a ring gear surrounding and inter-connecting each spur gear.

The contact port can accommodate receipt of contacts of varying cross-sectional profiles therein.

The universal contact port may further include at least one biasing member operatively associated with at least one of the ring gear, at least one of the spur gears and at least one of the rollers, wherein the biasing member urges the rollers into contact with one another.

The opening may be sizable to receive contacts having cross-sectional diameters from about 2 mm to about 10 mm.

According to yet another aspect of the present disclosure, an electrosurgical system including an electrosurgical generator, and an electrosurgical component including an active contact for operatively connecting the electrosurgical component to the electrosurgical generator is provided. The improvement includes a contact port operatively associated with the electrosurgical generator for receiving active contacts of varying cross-sectional diameters therein. The contact port includes a plurality of rollers each defining a corporal axis, the corporal axes being at least substantially parallel to one another; and a plurality of shafts eccentrically supporting a respective roller, each shaft defining a longitudinal axis, wherein each corporal axis is spaced a radial distance from a respective longitudinal axis and wherein the rollers are rotatable about the longitudinal axes. The rollers define an opening therebetween, wherein the opening is expandable and constrictable upon rotation of the rollers about their respective longitudinal axes.

The opening may have a minimum cross-sectional dimension when the rollers are in contact with one another. The opening may have a maximum cross-sectional profile when the corporal axes of the rollers are radially aligned with respective longitudinal axes of the shafts.

The contact port further includes a spur gear operatively associated with an end of each of the shafts; and a drive member operatively associated with all the spur gears for transmitting rotation to each of the spur gear simultaneously. The drive member may be a ring gear surrounding and inter-connecting each spur gear.

The contact port further includes at least one biasing member operatively associated with at least one of the ring gear, at least one of the spur gears and at least one of the rollers. The biasing member urges the rollers into contact with one another.

The electrosurgical component may be a foot switch.

The rollers of the contact port may be biased to a position wherein the opening is in a constricted condition. Each roller may include an electrical contact pad operatively disposed on a surface thereof.

The contact port may further include an actuator rod operatively associated with the rollers. Accordingly, movement of the actuator rod in a first direction moves the rollers in a direction so as to expand the opening therebetween, and movement of the actuator rod in a second direction moves the rollers in a direction so as to constrict the opening therebetween. The actuator rod includes a distal end projecting from the electrosurgical generator, and a proximal end pivotably supporting a first end of a lever. The contact port may further include a pusher member pivotably connected to a second end of the lever, wherein the lever pivots about a point located between the first and second ends thereof. Movement of the actuator rod in a first direction results in movement of the pusher member in a direction opposite to the first direction.

A distal end of the pusher member may operatively engage the rollers. Accordingly, movement of the pusher member in a direction towards the rollers results in radial movement of the rollers and radial expansion of the opening therebetween.

The electrosurgical system further includes an electrical lead electrically connected to each roller. The electrosurgical system further includes a housing configured and dimensioned to operatively retain the contact port therein.

According to still another aspect of the present disclosure, a universal contact port for use in an electrosurgical generator is provided. The contact port includes a housing defining an aperture for registration with an aperture formed in the electrosurgical generator; a plurality of rollers pivotally supported in the housing and pivotable about a pivot axis, each roller defining a corporal axis spaced a distance from the pivot axis, wherein the corporal axes of the rollers are parallel to one another, the rollers define an opening therebetween, wherein the opening is constricted by rotation of the rollers in a first direction about their respective pivot axes and expanded by rotation of the rollers in a second direction about their respective pivot axes; an actuator rod slidably supported in the housing, the actuator rod including a distal end extending from a distal end of the housing and projecting from the electrosurgical generator, and a proximal end projecting from a proximal end of the housing; a pusher member operatively associated with the housing, the pusher member including a distal in operative engagement with the rollers, wherein movement of the pusher member in a first direction causes the rollers to radially expand and the opening therebetween to radially expand, and wherein movement of the pusher member in a second direction causes the rollers to radially retract and the opening therebetween to radially constrict; and a lever pivotally interconnecting the proximal end of the actuator rod to a proximal end of the pusher member, wherein the lever is pivotally connected to the housing, wherein movement of the actuator rod in a first direction results in movement of the pusher member in the first direction and movement of the actuator rod in a second direction results in movement of the pusher member in the second direction.

The actuator rod may be biased in the second direction. The rollers may be biased to a radially constricted condition.

Each roller may include an electrical contact pad disposed on a surface thereof. The electrical contact pads may be positioned on the rollers so as to engage a contact of an electrosurgical accessory when the contact of the electrosurgical accessory is inserted into the opening between the rollers and the rollers constricted onto the contact of the electrosurgical accessory. Each roller may be configured for electrical connection with a respective electrical lead, and wherein each contact pad is in electrical communication with a respective electrical lead.

BRIEF DESCRIPTION OF THE DRAWINGS

Various embodiments of the present disclosure are described with reference to the following drawing figures. It should be understood, however, that the drawings are designed for the purpose of illustration only and not as a definition of the limits of the invention.

DETAILED DESCRIPTION

Figure 1:
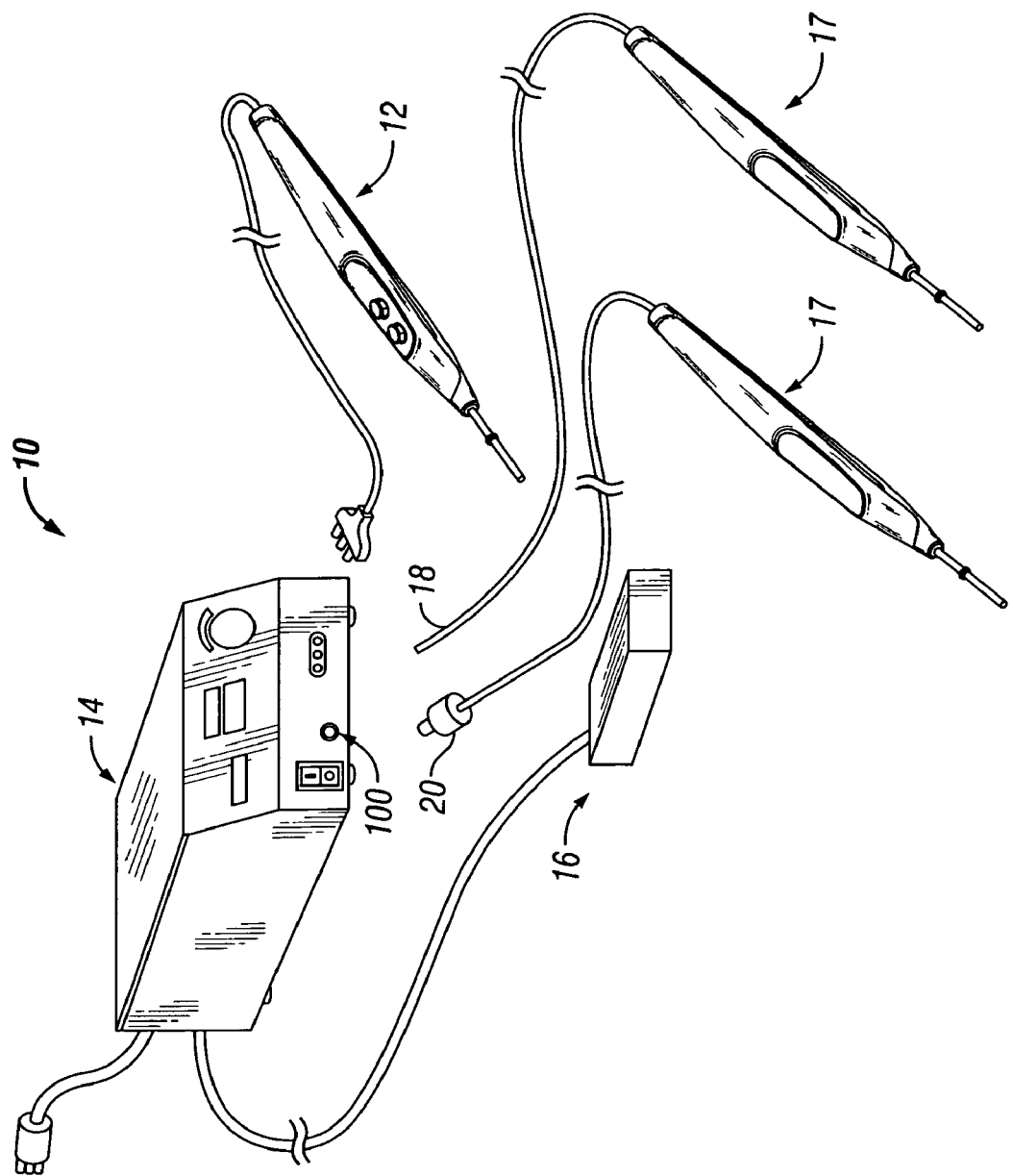
FIG. 1 is a schematic illustration of an electrosurgical instrument system including a universal contact port according to the present disclosure.

Embodiments of the presently disclosed universal contact port for electrosurgical generators are described in detail herein with reference to the drawing figures wherein like reference numerals identify similar or identical elements. In the drawings and in the description which follows, the term "proximal", as is traditional, will refer to the end of the apparatus and/or device which is closest to the operator, while the term "distal" will refer to the end of the apparatus and/or device which is furthest from the operator.

Referring initially to FIG. 1, there is seen a perspective view of an electrosurgical instrument system in accordance with an exemplary embodiment of the present disclosure, generally indicated as reference numeral 10. Electrosurgical instrument system 10 includes an electrosurgical instrument 12 (e.g., an electrosurgical pencil) which is electrically connectable to a source of electrosurgical energy 14 (e.g., an electrosurgical generator).

By way of example only, electrosurgical generator 14 may be any one of the following, or equivalents thereof: the "FORCE FX™", "FORCE 2™" or "FORCE 4™" generators manufactured by Valleylab, Inc. of Boulder, Colo., a division of Tyco Healthcare Group LP. It is contemplated that electrosurgical generator 14 can be preset to selectively provide an appropriate RF signals (e.g., about 1 to 300 watts) for a particular surgical procedure. Electrosurgical generator 14 may be adapted to automatically configure itself to transmit particular RF signals depending on the particular electrosurgical instrument connected thereto.

Electrosurgical instrument system 10 can further include a foot switch 16 which selectively couples to electrosurgical generator 14. Electrosurgical generator 14 includes a universal contact port 100 operatively associated therewith. Contact port 100 is configured to receive contacts 18 or plugs 20 of a foot-switched accessory 17. As understood herein, a foot-switched accessory is a surgical device that requires a separate foot switch 16 to activate electrosurgical generator 14 to provide the RF energy which is delivered to the patient through the foot-switched accessory 17. A foot-switched accessory 17 is similar to electrosurgical instrument 12 except that electrosurgical instrument 12 is hand-switched as opposed to foot-switched. In particular, contact port 100 is configured to accommodate receipt of and establish acceptable electrical connection with contacts 18 of varying diameters, e.g., from about 2 mm to about 10 mm.

With reference to FIGS. 2-5, contact port 100 functions in the manner of a planetary and/or epicyclical gear system. Contact port 100 includes a drive member in the form of a ring or sun gear 110, a plurality of spur gears 120a, 120b, 120c (i.e., planet gears) operatively associated with ring gear 110, and a plurality of rollers 130a, 130b, 130c operatively associated with a respective one of the plurality of spur gears 120a, 120b, 120c.

Ring gear 110 includes an annular body 112 defining a circular inner rim 114 having a plurality of gear teeth 116 formed therein. Gear teeth 116 extend at least partially, preferably entirely, around the perimeter of inner rim 114. Inner rim 114 of ring gear 110 defines a central rotational axis "X".

While a ring gear 100 surrounding spur gears 120 is shown, it is envisioned that a ring gear disposed radially internally of the spur gears is possible and within the scope of the present disclosure (not shown). In addition, while a rigid ring gear is shown, it is envisioned and within the scope of the present disclosure that a belt, band or chain (not shown) interconnecting all of the spur gears is also possible. It is further envisioned that each spur gear 120 may be configured for independent rotation. Preferably, the system is configured to result in simultaneous uniform rotation of spur gears 120 to assume consistent and reliable electromechanical connection of contact 18 or plug 20.

Preferably, contact port 100 includes three spur gears 120a, 120b and 120c. While three spur gears are shown, it is envisioned that any number of spur gears can be provided depending on the particular purpose. Preferably, spur gears 120a, 120b and 120c are each supported on a first end 122 of a respective shaft 124a, 124b and 124c. Each spur gear 120a, 120b and 120c includes a series of teeth 128 for meshing with and/or otherwise inter-engaging with gear teeth 116 of ring gear 110. Spur gears 120a, 120b and 120c are preferably fixedly connected to respective shafts 124a, 124b and 124c. In this manner, as will be discussed in greater detail below, as spur gears 120a, 120b and 120c are rotated, shafts 124a, 124b and 124c are also rotated.

Preferably, a second end 126 of each shaft 124a, 124b and 124c is rotatably supported and/or is otherwise operatively associated with the inner surface of electrosurgical generator 14. Each shaft 124a, 124b and 124c defines a central longitudinal axis "Xa, Xb and Xc", respectively. Preferably, central longitudinal axes "Xa, Xb and Xc" are at least substantially parallel with central axis "X" of ring gear 110.

Shafts 124a, 124b and 124c are positioned such that spur gears 120a, 120b and 120c are preferably equi-distant from one another, e.g., spaced from one another by about 120°.

Contact port 100 includes three rollers 130a, 130b and 130c, eccentrically supported on a respective shaft 124a, 124b and 124c. Rollers 130a, 130b and 130c define an opening 140 therebetween.

Rollers 130a, 130b and 130c are substantially cylindrical in configuration and define central corporal axes "Wa, Wb and Wc", respectively. Each central corporal axis "Wa, Wb and Wc" of roller 130a, 130b and 130c is parallel to and preferably offset a radial distance from the central longitudinal axis Xa, Xb and Xc of each respective shaft 124a, 124b and 124c. In operation, as will be discussed in greater detail below, as shafts 124a, 124b and 124c are rotated about respective central axes "Xa, Xb and Xc", rollers 130a, 130b and 130c are approximated toward one another to constrict opening 140 (or space apart from one another to expand opening 140).

Figure 2:
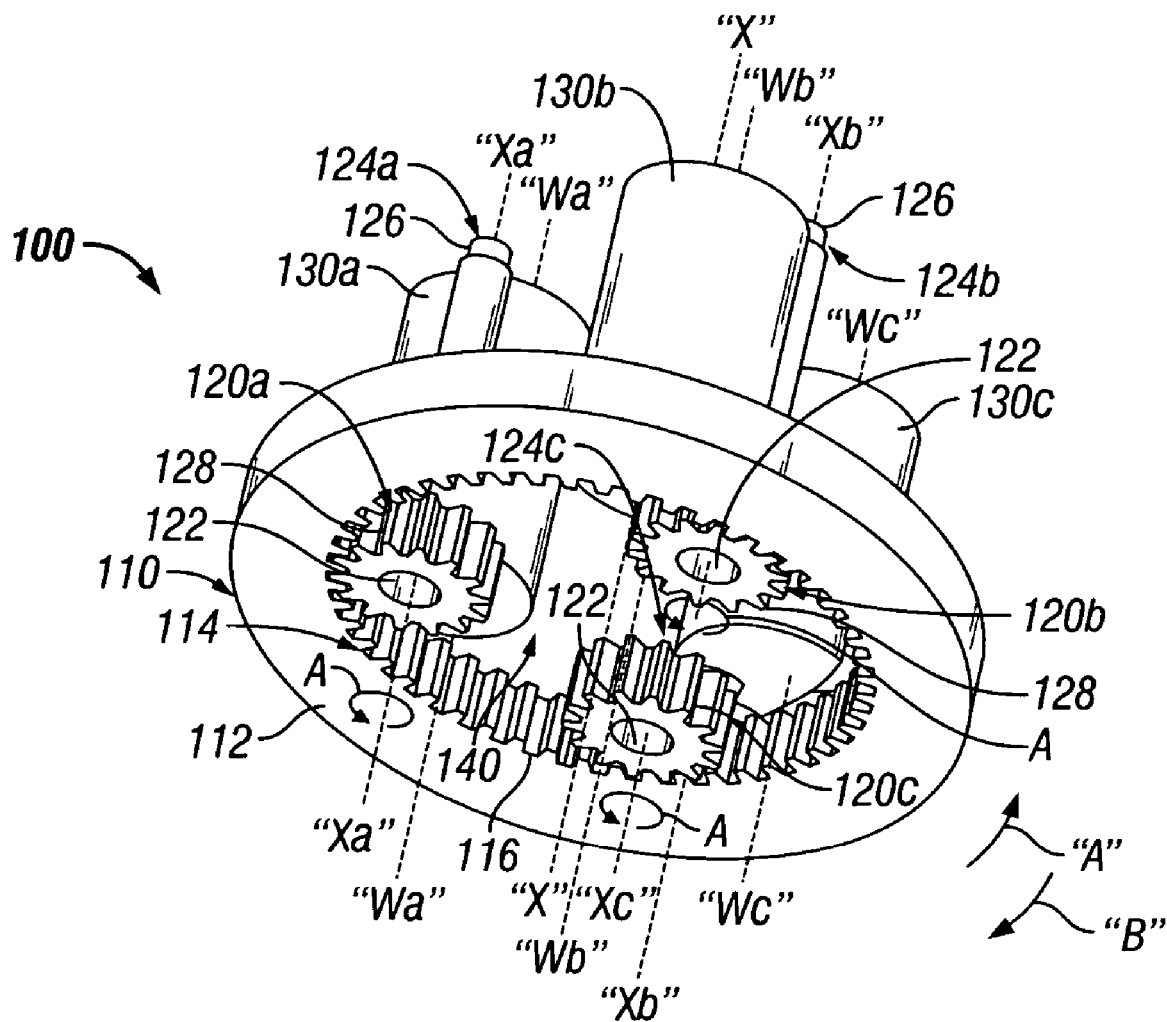
FIG. 2 is an enlarged perspective view of the universal contact port of the present disclosure.
Figure 3:
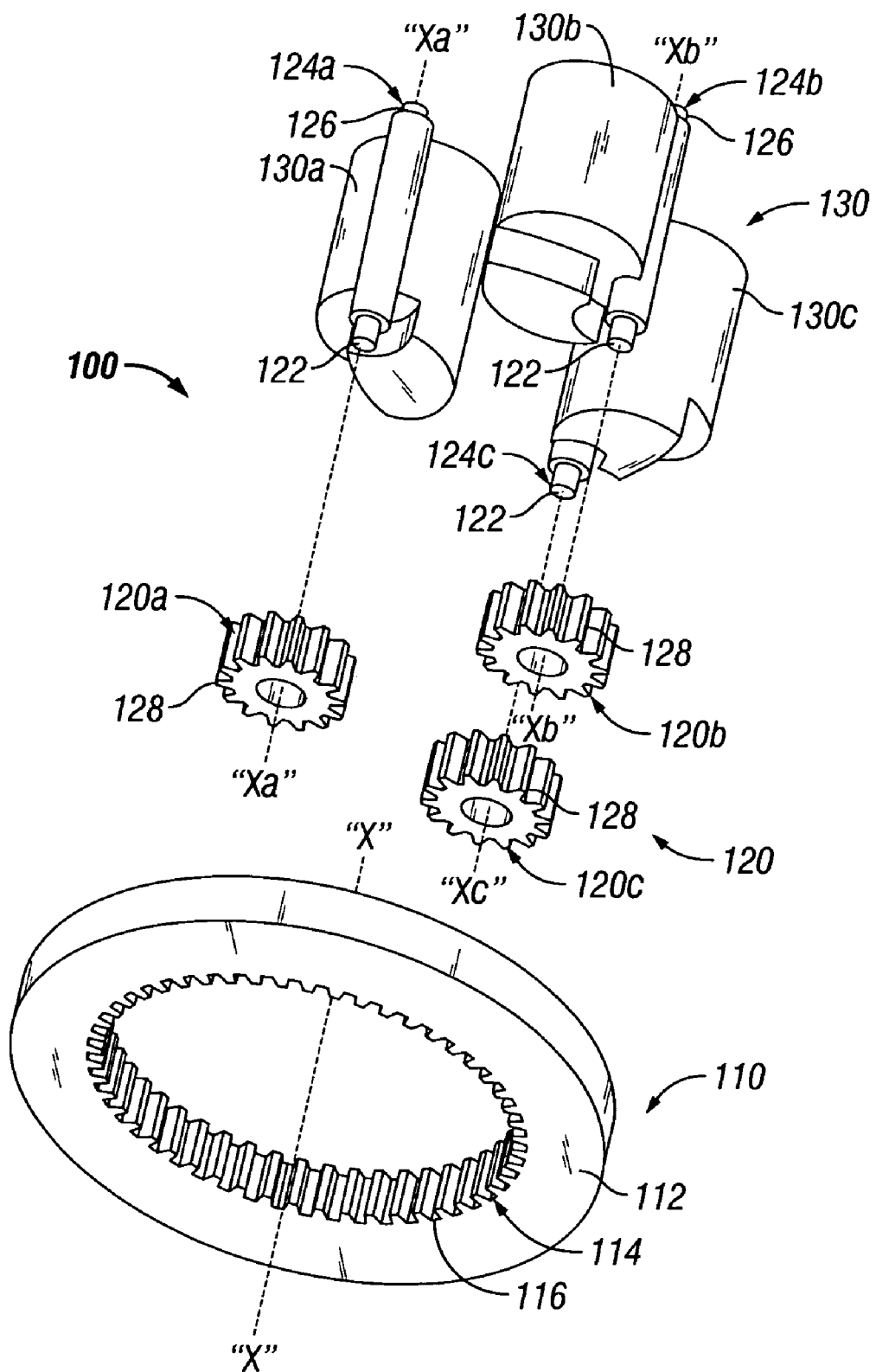
FIG. 3 is an enlarged exploded perspective view of the universal contact port of FIG. 2.
Figure 4:
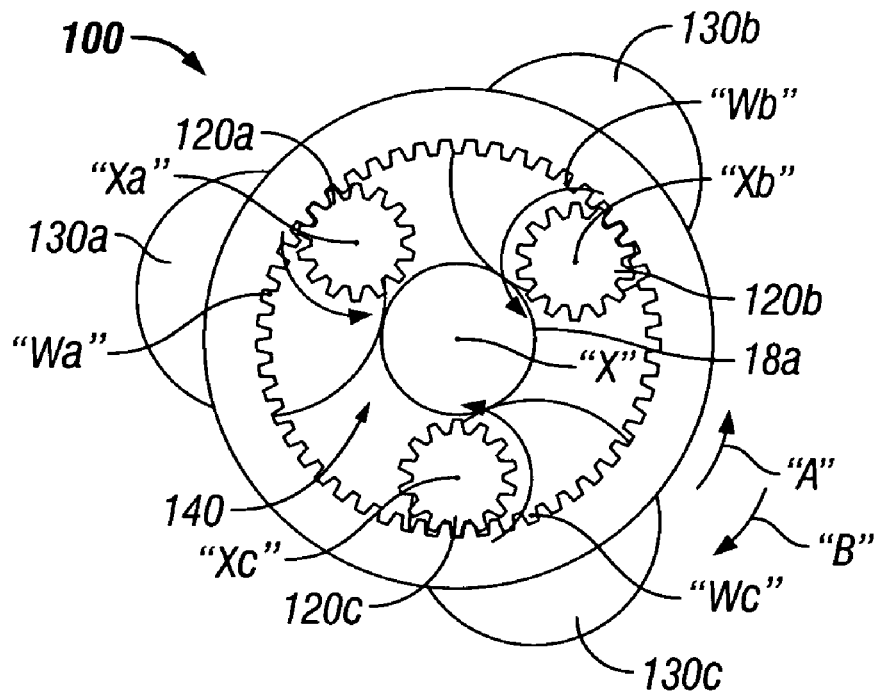
FIG. 4 is a schematic elevational view of universal contact port of FIGS. 2 and 3, illustrating the inter-engagement of the contact port with an active contact having a relatively large cross-sectional diameter.
Figure 5:
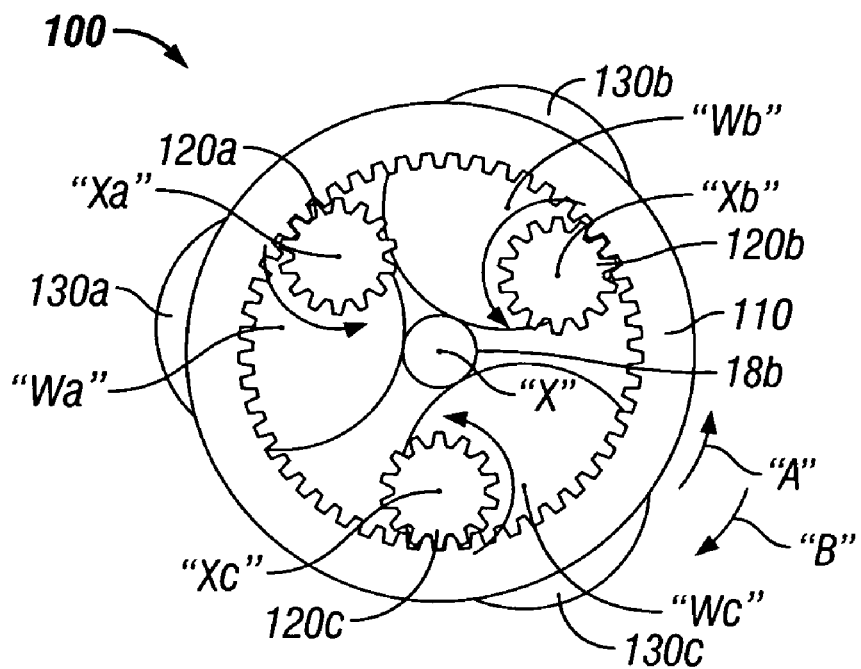
FIG. 5 is a schematic elevational view of the universal contact port of FIGS. 2-4, illustrating the inter-engagement of the contact port with an active contact having a relatively small cross-sectional diameter.

In operation, as seen in FIGS. 2, 4 and 5, as ring gear 110 is rotated about central axis "X" in the direction of arrow "A" (i.e., in a counter-clockwise direction), each spur gear 120a, 120b and 120c rotates about respective axes "Xa, Xb and Xc", in direction "A" (i.e., in a counter-clockwise direction). In so doing, rollers 130a, 130b and 130c are approximated toward one another thereby constricting opening 140. Additionally, as ring gear 110 is rotated about central axis "X" in the direction of arrow "B" (i.e., in a clockwise direction), each spur gear 120a, 120b and 120c rotates about respective axes "Xa, Xb and Xc", in direction "B" (i.e., in a clockwise direction). In so doing, rollers 130a, 130b and 130c separate from one another thereby causing opening 140 to expand.

It should be apparent to one skilled in the art that if ring gear 110 is continually rotated about central axis "X", in direction "B", rollers 130a, 130b and 130c will continue to rotate about axes "Xa, Xb and Xc" until the eccentricities of rollers 130a, 130b and 130c revert to restricting opening 140.

With reference to FIG. 4, prior to insertion of contact 18 or plug 20 into opening 140, ring gear 110 is caused to be rotated in direction "B" to expand opening 140 to a dimension sufficient to receive contact 18 or plug 20 therein. Following insertion of a contact having a relatively large cross-sectional diameter into opening 140, e.g., contact 18a, ring gear 110 is rotated (or caused to be rotated) in direction "A" to thereby constrict opening 140. In other words, ring gear 110 is rotated in direction "A" until rollers 130a, 130b and 130c engage contact 18a.

With reference to FIG. 5, following insertion of a contact having a relatively small cross-sectional diameter into opening 140, e.g., contact 18b, ring gear 110 is rotated (or caused to be rotated) in direction "A" the thereby constrict opening 140. As can be appreciated, since contact 18b has a relatively smaller cross-sectional diameter than contact 18a, ring gear 110 is necessarily rotated further in direction "A" until rollers 130a, 130b and 130c properly engage contact 18b.

Preferably, contact port 100 can accommodate receipt of contacts 18 having diameters from about 2 mm to about 10 mm. It is envisioned that contact 18 may include diameters which are in a range defined from when rollers 130a, 130b and 130c are almost in substantial contact with one another to a diameter when axes "Wa, Wb and Wc" of rollers 130a, 130b and 130c are spaced the greatest radial distance from central axis "X" of ring gear 110.

In other words, the acceptable diameter of contact 18 is at a minimum when rollers 130a, 130b and 130c are in contact with one another. The acceptable diameter of contact 18 is at a maximum when corporal axes "Wa, Wb and Wc" of rollers 130a, 130b and 130c are positioned radially outward of longitudinal axes "Xa, Xb and Xc" of shafts 124a, 124b and 124c relative to central rotational axis "X".

Preferably, rollers 130a, 130b and 130c are biased toward one another by a biasing member, e.g., a spring, (not shown). In this manner, rollers 130a, 130b and 130c can be urged, against the force of the biasing member, apart from one another. Then, following insertion of contact 18 into opening 140, rollers 130a, 130b and 130c automatically return or bias toward one another as a result of force of the biasing member. The force of the biasing member can be applied to ring gear 110, to at least one of spur gears 120a, 120b and 120c, and/or to at least one of rollers 130a, 130b and 130c.

Contact port 100 preferably includes a button, lever or mechanism (not shown) which drives ring gear 110 against the force of the biasing member to thereby expand opening 140. Following insertion of contact 18 into opening 140 the button is released and the rollers constrict around contact 18, as described in detail above. In order to remove contact 18, the button is depressed in order to rotate ring gear 110 in the appropriate direction to cause opening 140 to expand thereby electro-mechanically releasing. By way of example only, the button may include a worm gear or the like formed in a proximal end thereof which engages or meshes with a complementary gear formed along the outer edge of ring gear 110. Accordingly, when the button is pushed in ring gear 110 is rotated in the appropriate direction to thereby expand opening 140. It is further envisioned that the button may be spring biased to the ejected condition. In this manner, when the button is released, the button will be forced back to the non-pushed-in condition, thereby constricting opening 140.

While a planetary gear system is preferred, it is envisioned that a system of pins and slider elements may be used to cause rollers 130a, 130b and 130c to rotate. For example, this alternate system may include a link member having a first end pivotally connected to the housing of electrosurgical generator 14 and a second end operatively connected to a respective roller 130a, 130b and 130c. Desirably, each link may pivot about its first end to impart the desired motion to rollers 130a, 130b and 130c. The links may be joined together by pins operatively connected thereto that slide or translate in a groove or slot formed in the link. In this manner, as the pins are moved, the links are moved in concert to expand or constrict opening 140.

Preferably, rollers 130a, 130b and 130c are fabricated from electrically conductive material, e.g., stainless steel, and are each disposed in electrical connection with electrosurgical generator 14. In this manner, when contact 18 is inserted into contact port 100, electrical connection is established between contact 18 of plug 20 and electrosurgical generator 14, via rollers 130a, 130b and 130c. Alternatively, electrical connection can be established through the gear train.

Contact port 100 eliminates the need to use an adapter to establish a connection between a plug having a contact of a given dimension and a plug receptacle having a dimension different from that of the contact.

Moreover, contact port 100 allows for electrical connections to be established with contacts having any number of cross-sectional profiles, including and not limited to, square, rectangle, L-shaped, elliptical, oblong, circular, etc.

Figure 6:
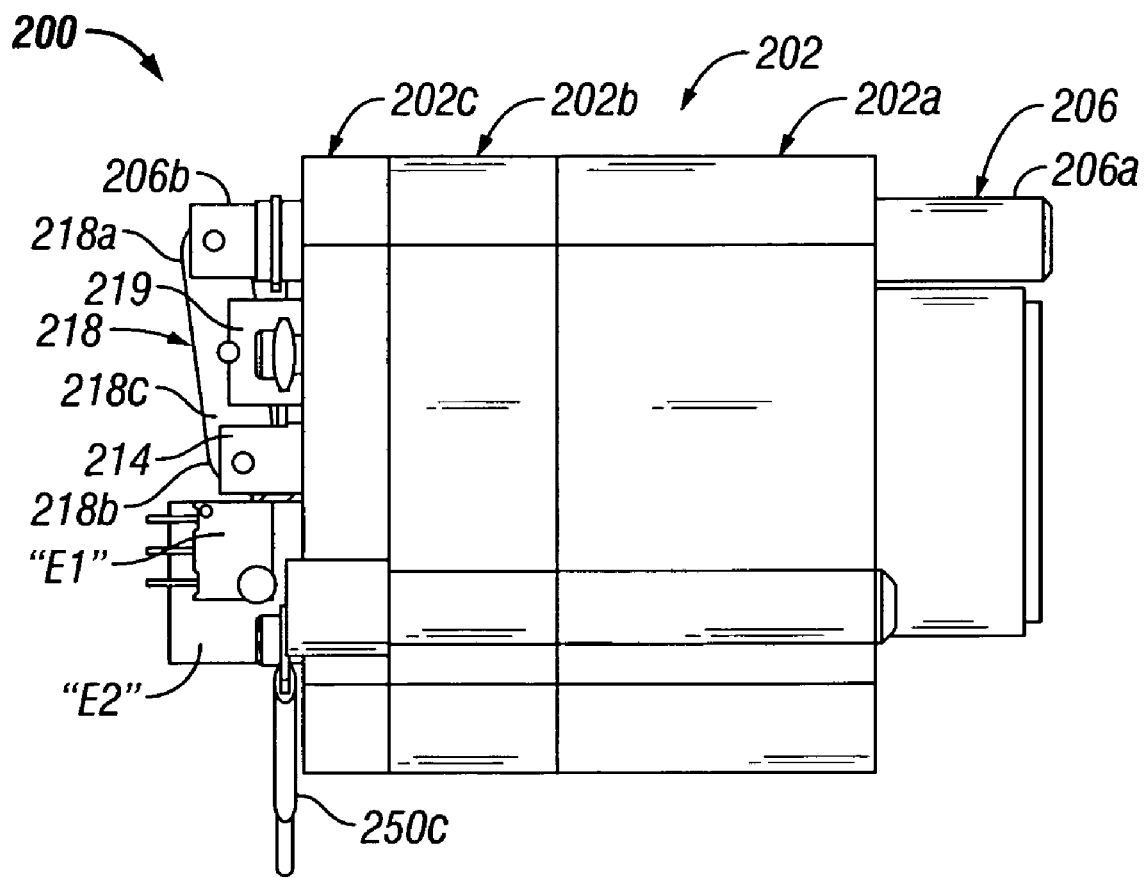
FIG. 6 is a side elevational view of a universal contact port according to another embodiment of the present disclosure.

Various dimensions for ring gear 110 and for spur gears 120a, 120b, 120c are shown in Table A shown in FIG. 6. For example, in one embodiment, ring gear 110 may have an inner diameter of about 0.375 inches, each longitudinal axis "Xa, Xb, and Xc" of spur gears 120a, 120b and 120c may be offset about 0.106 inches from the longitudinal "X" axis, and each spur gear 120a, 120b and 120c may have a diameter of about 0.063 inches to about 0.125 inches.

Turning now to FIGS. 6-11, a universal contact port according to another embodiment of the present disclosure is generally designated as 200. Universal contact port 200 includes a housing 202 including a distal portion 202a, a middle portion 202b, and a proximal portion 202c. Housing 202 is desirably mounted to an inner surface of electrosurgical generator 14. Housing 202 includes an aperture 204 provided in distal portion 202a which is in registration with an opening provided in electrosurgical generator 14. Aperture 204 is configured to receive contacts 18 or plug 20 of a foot-switched accessory 17. (see FIG. 1).

Universal contact port 200 further includes a drive member 206, in the form of an actuator rod, extending through housing 202. Desirably, a distal end 206a of actuator rod 206 projects from or extends through distal portion 202a of housing 202 and through the wall of electrosurgical generator 14. A proximal end 206b of actuator rod 206 extends through proximal portion 202c of housing 202 and defines a clevis 208 or the like.

Figure 7:
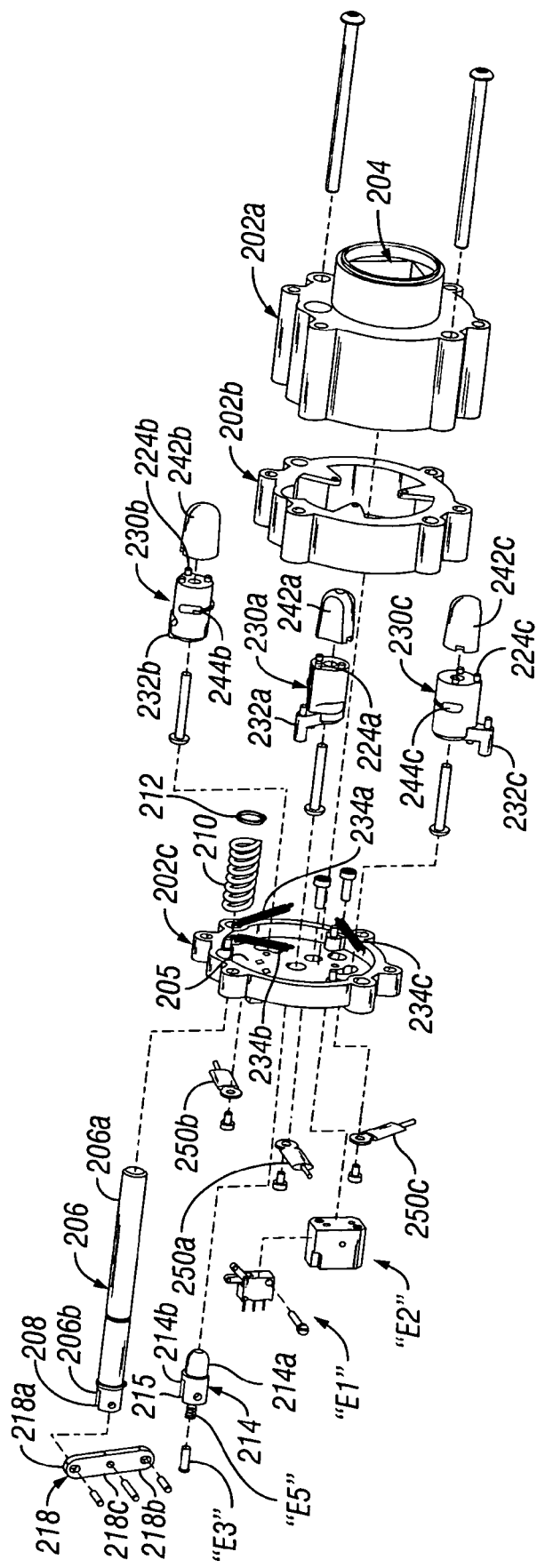
FIG. 7 is a perspective view, with parts separated, of the universal contact port of FIG. 6.
Figure 8:
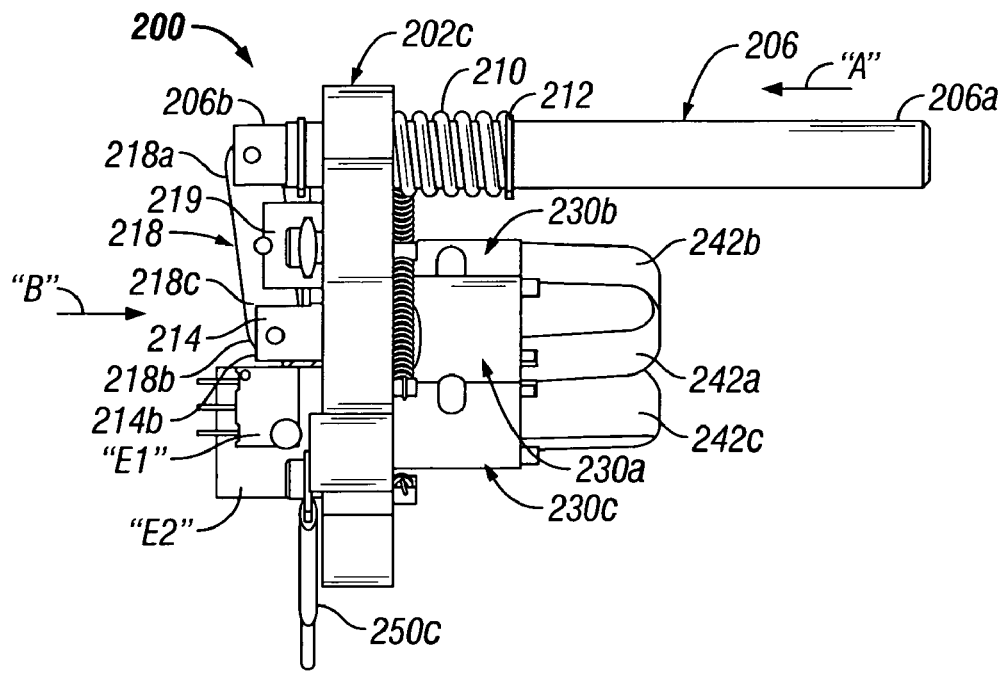
FIG. 8 is a side elevational view of the universal contact port of FIGS. 6 and 7, with the housing removed therefrom.
Figure 11:
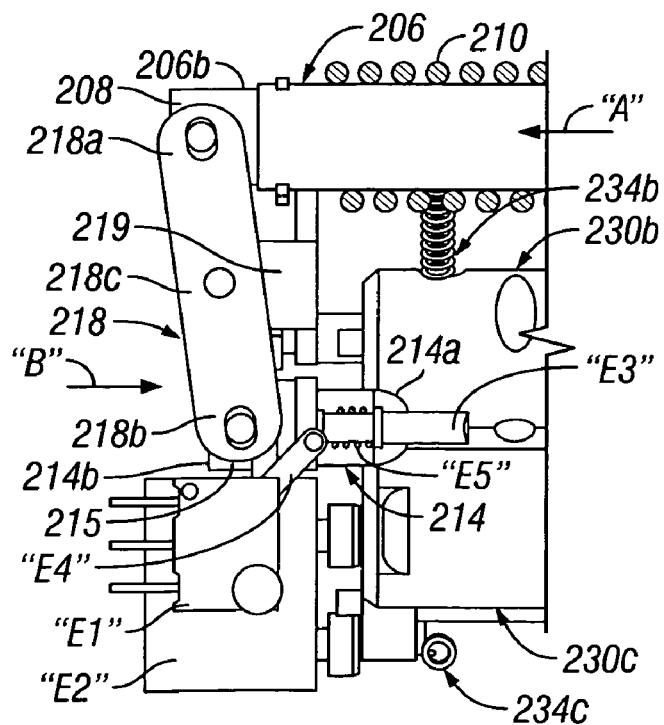
FIG. 11 is a longitudinal cross-sectional view of the universal contact port of FIGS. 6-9, as taken through 11-11 of FIG. 9.

Desirably, as seen in FIGS. 7, 8 and 11, actuator rod 206 is biased to a first un-actuated or un-pressed condition by a biasing member 210 (e.g., a compression spring) or the like. In one embodiment, biasing member 210 is disposed between an inner surface of proximal portion 202c of housing 202 and a C-clamp 212 operatively connected to actuator rod 206.

Universal contact port 200 further includes a pusher member 214 slidably positioned in a central aperture 216 (see FIG. 7) formed in proximal portion 202c of housing 202. Pusher member 214 includes a tapered distal end portion 214a and a proximal end portion 214b defining a clevis 215.

Universal contact port 206 includes a link member 218 operatively interconnecting clevis 208 of actuator rod 206 and to clevis 215 of pusher member 214. Desirably, a first end 218a of link member 218 is pivotally connected to clevis 208 of actuator rod 206 and a second end 218b of link member 218 is pivotally connected to clevis 215 of pusher member 214. Desirably, a central portion 218c of link member 218 is pivotally connected to a stem 219 projecting from proximal portion 202c of housing 202. In this manner, as will be described in greater detail below, as actuator rod 206 is pressed or moved in a proximal direction, as indicated by arrow "A" of FIGS. 9 and 11, link member 218 causes pusher member 214 to move in a distal direction, as indicated by arrow "B" of FIGS. 8 and 11.

Figure 9:
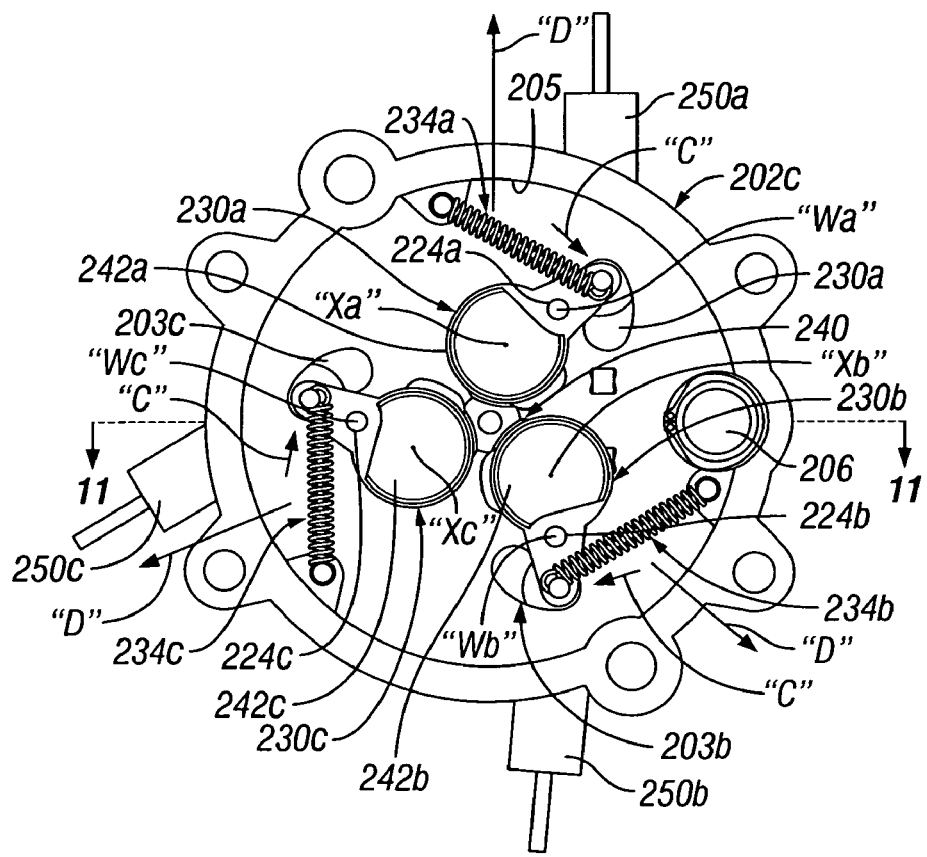
FIG. 9 is a rear elevational view of the universal contact port of FIGS. 6-8, with the housing removed therefrom.
Figure 10:
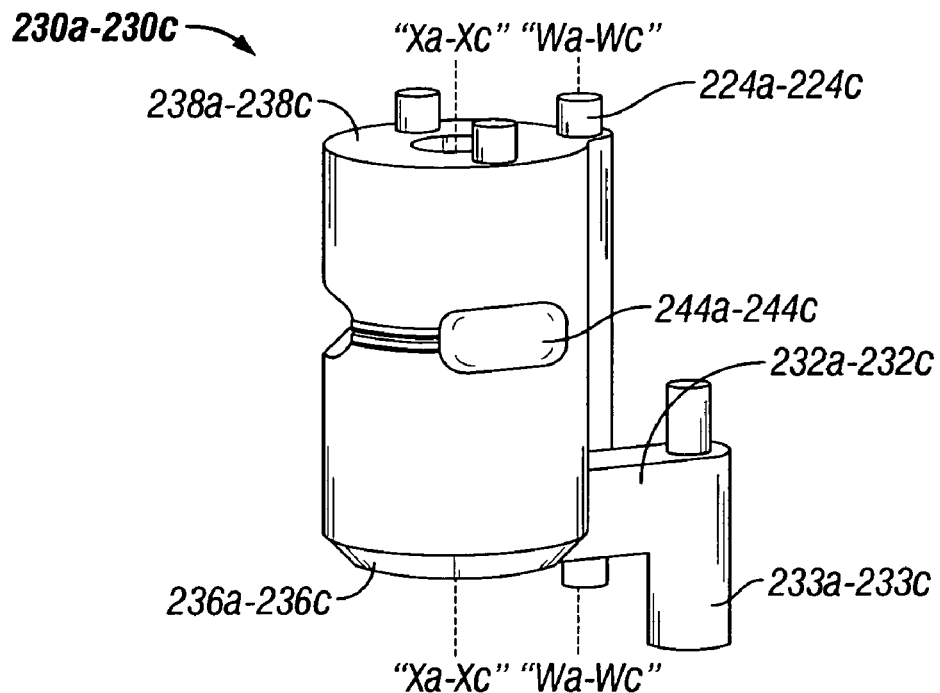
FIG. 10 is a perspective view of a roller of the universal contact port of FIGS. 6-9.

Universal contact port 200 further includes a plurality of rollers 230a-230c eccentrically pivotally supported within housing 202. Desirably, rollers 230a-230c are pivotally supported between middle portion 202b and proximal portion 202c of housing 202. As seen in FIGS. 9 and 10, each roller 230a-230c is substantially cylindrical in configuration and defines a central longitudinal axis "Xa-Xc", respectively.

As seen in FIGS. 7, 9 and 10, each roller 230a-230c includes a shaft or pivot rod 224a-224c, respectively, each defining an axis "Wa-Wc", respectively, about which rollers 230a-230c rotate. Desirably, shafts 224a-224c are pivotally supported in receiving holes or apertures formed in proximal portion 202c and middle portion 202b of housing 202.

As seen in FIG. 9, when rollers 230a-230c are supported in housing 202, rollers 230a-230c define an opening 240 therebetween. Rollers 230a-230c are pivotable between a first position in which rollers 230a-230c are in relative close proximity to one another (i.e., opening 240 is in a constricted condition), and a second position in which rollers 230a-230c are relatively spaced from one another (i.e., opening 240 is in an expanded condition).

As seen in FIGS. 7-10, each roller 230a-230c includes a respective actuation arm 232a-232c extending radially therefrom. As will be described in greater detail below, in operation, as actuation arms 232a-232c are moved in a first direction, as indicated by arrows "C" of FIG. 9, rollers 230a-230c pivot about pivot axes "Wa-Wc" in a second direction, as indicated by arrows "D" of FIG. 9, thereby expanding opening 240. Additionally, it follows that as rollers 230a-230c are pivoted about pivot axes "Wa-Wc", as indicated by arrows "D", thereby expanding opening 240, actuation arms 232a-232c are moved in the direction of arrows "C".

Universal contact port 200 includes a plurality of biasing members 234a-234c (e.g., springs) extending between and connecting a respective actuation arm 232a-232c of rollers 230a-230c to proximal portion 202c of housing 202. In this manner, biasing members 234a-234c maintain rollers 230a-230c in a biased first or constricted condition (i.e., opening 240 is in the constricted condition).

In use, as will be described in greater detail below, when rollers 230a-230c are forced to move in the direction of arrow "D" by movement of pusher member 214 in the direction of arrow "B" (i.e., into opening 240), thereby expanding opening 240, biasing members 234a-234c are stretched or biased. Accordingly, upon movement of pusher member 214 in a direction opposite to arrow "B" (i.e., out of opening 240), biasing members 234a-234c retract, thereby causing rollers 230a-230c to move in a direction opposite to arrow "D" and thus constrict opening 240.

Desirably, as seen in FIG. 10, each roller 230a-230c includes a tapered or angled annular proximal surface 236a-236c, respectively. In operation, when pusher member 214 is moved in a distal direction, tapered distal end portion 214a of pusher member 214 engage and/or cam against tapered proximal surfaces 236a-236c of rollers 230a-230c to radially expand opening 240.

Each roller 230a-230c desirably includes a cap 242a-242c, respectively, operatively connected to or supported on a respective distal end 238a-238c thereof. Each cap 242a-242c may have a tapered configuration or the like.

As seen in FIGS. 7, 9 and 10, each roller 230a-230c includes an electrical contact pad 244a-244c, respectively. Desirably, contact pads 244a-244c are disposed along a side surface of rollers 230a-230c. Preferably, contact pads 244a-244c are positioned on rollers 230a-230c such that contact pads 244a-244c are oriented towards opening 240. In use, as will be described in greater detail below, when contact 18 or plug 20 is inserted into opening 240 and rollers 230a-230c move into contact with contact 18 or plug 20, at least one contact pad 244a-244c, preferably each contact pad 244a-244c, is in electrical engagement with contact 18 or plug 20. When contact pads 244a-244c electrically engage contact 18 or plug 20, an electrical connection between electrosurgical generator 14 and accessory 17 is established.

As seen in FIGS. 7 and 10, each actuation arm 232a-232c of rollers 230a-230c includes a leg 233a-233c, respectively, extending in a proximal direction therefrom. Desirably, each leg 233a-233c extends through a respective slot 203a-203c formed in a rear surface 205 of proximal portion 202c of housing 202.

As seen in FIGS. 6-9, electrical leads 250a-250c are connected to a respective leg 233a-233c of rollers 230a-230c. Desirably, electrical leads 250a-250c are in electrical communication with contact pads 244a-244c of rollers 230a-230c.

As seen in FIGS. 6-8 and 11, universal contact port 200 includes a probe detection switch "E1" operatively supported on proximal portion 202c of housing 202 by a detection switch bracket "E2". Detection switch "E1" functions to alert electrosurgical generator 14 when a particular probe (e.g., contact 18, plug 20, etc.) is operatively connected to universal contact port 200.

In operation, when either contact 18 or plug 20 is inserted into opening 240 of housing 202, a distal end of contact 18 or plug 20 engages (i.e., pushes against) an detection switch actuator pin "E3" which in turn actuates a switch lever arm "E4". Actuation of lever arm "E4" may in turn actuate closure of rollers 230a-230c.

Desirably, a spring "E5" is provided to biasing and/or maintaining actuator pin "E3" and, in turn, lever arm "E4" in an un-actuated condition, thus maintaining rollers 230a-230c in an open condition.

With reference to FIGS. 6-11, a method of using universal contact port 200, for electrically connecting accessory 17 to electrosurgical generator 14, is shown and described. In order to electrically connect accessory 17 to electrosurgical generator 14, actuator rod 206 is pressed and held (i.e., moved in the direction of arrow "A" in FIG. 8) in order to radially expand opening 240 between rollers 230a-230c. In particular, as actuator rod 206 is pressed in the direction of arrow "A", pusher member 214 is moved in a distal direction (i.e., in the direction of arrow "B"), as described in detail hereinabove. Pressing of actuation rod 206 in the proximal direction also results in compression of biasing member 210.

As pusher member 214 moves in the distal direction, tapered distal end portion 214a thereof contacts and/or engages tapered annular surfaces 236a-236c of rollers 230a-230c and forces rollers 230a-230c in a radially outward direction, as indicated by arrows "D" of FIG. 9, thereby radially expanding opening 240. By moving rollers 230a-230c in a radially outward direction, biasing member's 234a-234c are stretched, as described in detail hereinabove.

With opening 240 radially expanded, contact 18 or plug 20 of accessory 17 is inserted into opening 240 through aperture 204 (see FIG. 7) of housing 202. Once contact 18 or plug 20 is inserted into opening 240, actuation rod 206 is released. Upon releasing actuation rod 206, biasing member or compression spring 210 is free to expand, thereby forcing actuation rod 206 in a distal direction and thereby forcing pusher member 214 in a proximal direction. As pusher member 214 is forced or moved in a proximal direction, distal end 214a of pusher member 214 is withdrawn from opening 240 (i.e., withdrawn from between rollers 230a-230c).

As pusher member 214 is withdrawn from opening 240, biasing member's 234a-234c contract, thereby rotating rollers 230a-230c about their respective pivot axes "Wa-Wc" and constricting opening 240. As opening 240 is constricted, contact pads 244a-244c of respective rollers 230a-230c electrically engage contact 18 or plug 20 thereby completing the electrical connection of accessory 17 to electrosurgical generator 14.

Following the surgical procedure, accessory 17 may be disconnected from electrosurgical generator 14 by simply pulling on contact 18 or plug 20 to thereby withdraw contact 18 or plug 20 from universal contact port 200, or, alternatively, actuation rod 206 may be pressed so as to radially expand opening 240 and thus disengage rollers 230a-230c from contact 18 or plug 20 allowing for contact 18 or plug 20 to be withdrawn from opening 240.

Universal contact ports 100 and 200 enable contacts 18 and/or plugs 20 having a variety of transverse cross-section profiles to be electrically connected to electrosurgical generator 14. For example, contacts 18 or plugs 20 having circular, rectangular, triangular, symmetrical, non-symmetrical, "L-shaped", "V-shaped" and any combination thereof, may be electrically connected to electrosurgical generator 14 using universal contact ports 100 or 200.

It is envisioned and it is in accordance with an embodiment of the present disclosure, that only one of contact pads 244a-244c needs to touch and/or electrically engage contact 18 or plug 20 in order to establish a sufficient electrical connection for operation of accessory 17.

From the foregoing and with reference to the various figure drawings, those skilled in the art will appreciate that certain modifications can also be made to the present disclosure without departing from the scope of the present disclosure.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments.

Those skilled in the art will envision other modifications within the scope and spirit of the claims appended hereto.

The invention claimed is:

1. A universal contact port for receiving contacts of various cross-sectional dimensions and cross-sectional profiles of an electrosurgical component, the universal contact port comprising:
   a plurality of rollers each defining a corporal axis, the corporal axes being at least substantially parallel to one another; and
   a plurality of shafts eccentrically supporting a respective roller, each shaft defining a longitudinal axis, wherein each corporal axis is spaced a radial distance from a respective longitudinal axis and wherein the rollers are rotatable about the longitudinal axes;
   the rollers defining an opening therebetween, wherein the opening is expandable and constrictable upon rotation of the rollers about the longitudinal axes, whereby the contact port can accommodate receipt of contacts, from electrosurgical components, of varying cross-sectional diameter therein,
   wherein the rollers of the contact port are biased to a position wherein the opening is in a constricted condition,
   wherein each roller includes an electrical contact pad operatively disposed on a surface thereof.

2. The universal contact port according to claim 1, wherein the opening has a minimum cross-sectional dimension when the rollers are in contact with one another.

3. The universal contact port according to claim 2, wherein the opening has a maximum cross-sectional profile when the corporal axes of the rollers are radially aligned with respective longitudinal axes of the shafts.

4. In an electrosurgical system including an electrosurgical generator, and an electrosurgical component including an active contact for operatively connecting the electrosurgical component to the electrosurgical generator, the improvement comprising:
   a contact port operatively associated with the electrosurgical generator for receiving active contacts of varying cross-sectional diameters therein, the contact port comprising:
   a plurality of rollers each defining a corporal axis, the corporal axes being at least substantially parallel to one another; and
   a plurality of shafts eccentrically supporting a respective roller, each shaft defining a longitudinal axis, wherein each corporal axis is spaced a radial distance from a respective longitudinal axis and wherein the rollers are rotatable about the longitudinal axes;
   the rollers defining an opening therebetween, wherein the opening is expandable and constrictable upon rotation of the rollers about their respective longitudinal axes,
   wherein the rollers of the contact pod are biased to a position wherein the opening is in a constricted condition,
   wherein each roller includes an electrical contact pad operatively disposed on a surface thereof.

5. The electrosurgical system according to claim 4, wherein the opening has a minimum cross-sectional dimension when the rollers are in contact with one another.

6. The electro surgical system according to claim 5, wherein the opening has a maximum cross-sectional profile when the corporal axes of the rollers are radially aligned with respective longitudinal axes of the shafts.

7. The electrosurgical system according to claim 4, wherein the contact port further includes an actuator rod operatively associated with the rollers, wherein movement of the actuator rod in a first direction moves the rollers in a direction so as to expand the opening therebetween, and movement of the actuator rod in a second direction moves the rollers in a direction so as to constrict the opening therebetween.

8. The electrosurgical system according to claim 7, wherein the actuator rod includes a distal end projecting from the electrosurgical generator, and a proximal end pivotably supporting a first end of a lever, the contact port further includes a pusher member pivotably connected to a second end of the lever, wherein the lever pivots about a point located between the first and second ends thereof.

9. The electrosurgical system according to claim 8, wherein movement of the actuator rod in a first direction results in movement of the pusher member in a direction opposite to the first direction.

10. The electrosurgical system according to claim 9, wherein a distal end of the pusher member operatively engages the rollers, wherein movement of the pusher member in a direction towards the rollers results in radial movement of the rollers and radial expansion of the opening therebetween.

11. The electrosurgical system according to claim 10, further comprising an electrical lead electrically connected to each roller.

12. The electrosurgical system according to claim 11, further comprising a housing configured and dimensioned to operatively retain the contact port therein.

* * * * *